United States Patent [19]

Plum et al.

[11] 4,108,990
[45] Aug. 22, 1978

[54] METHOD OF KILLING BACTERIA AND FUNGI

[75] Inventors: Hans Plum, Heessen; Max Buschhoff, Luenen; Alena Cejka, Dortmund, all of Fed. Rep. of Germany

[73] Assignee: Schering Aktiengesellschaft, Berlin and Bergkamen, Fed. Rep. of Germany

[21] Appl. No.: 695,125

[22] Filed: Jun. 11, 1976

[30] Foreign Application Priority Data

Jun. 14, 1975 [DE] Fed. Rep. of Germany ....... 2526711
Mar. 16, 1976 [DE] Fed. Rep. of Germany ....... 2610931

[51] Int. Cl.² .............................................. A01N 9/12
[52] U.S. Cl. ......................... 424/245; 106/15 R; 424/288; 424/357
[58] Field of Search ................................... 424/288

[56] References Cited

U.S. PATENT DOCUMENTS

| | | | |
|---|---|---|---|
| 2,867,566 | 1/1959 | Weinberg | 260/429.7 |
| 3,037,039 | 5/1962 | Mazur | 424/288 |
| 3,344,019 | 9/1967 | Sowa | 424/288 |
| 3,755,595 | 8/1973 | Goring et al. | 424/288 |
| 3,763,198 | 10/1973 | Flannigan et al. | 424/288 X |

FOREIGN PATENT DOCUMENTS 945,068 12/1963 United Kingdom ..................... 424/288

OTHER PUBLICATIONS

Srivastava et al., Journal of Inorganic Nuclear Chemistry, 4/1974, vol. 36, No. 4, pp. 733–736.
Zschunke et al., J. Org. Chem., 1973, vol. 51, pp. 197–201.
Davies, et al., J. Org. Chem., 1972, vol. 39, pp. 279–288.

*Primary Examiner*—Dale R. Ore
*Attorney, Agent, or Firm*—Curtis, Morris & Safford

[57] ABSTRACT

Biocidal agents containing as the active ingredients a diorgano tin compound of the formula

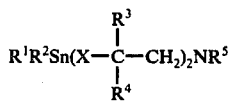

wherein $R^1$, $R^2$, $R^3$, $R^4$, and $R^5$ are various organic groups, ($R^3 + R^4$) may be oxygen, and X is oxygen or sulfur; methods for using such agents to kill bacteria and fungi, for example by treating a substrate such as wood or a textile with such agents; a method for making said diorgano tin compounds; and certain of said diorgano tin compounds as novel compositions of matter, are disclosed.

14 Claims, No Drawings

METHOD OF KILLING BACTERIA AND FUNGI

The present invention relates to di-organo tin compounds having bactericidal and fungicidal properties, to bactericidal and fungicidal agents containing these compounds, and to methods for making and using these compounds and agents.

It has long been known in the art that triorgano tin compounds have a high activity against harmful fungi and bacteria. Therefore these materials, particularly tributyl- and triphenyl-tin compounds, are today used in large amounts, for example as disinfecting agents and as protective agents for wood.

The highly effective triorgano tin compounds nevertheless have several disadvantages which strongly limit their use in particular fields. They show a considerable toxicity for warm blooded animals and, particularly, can produce skin irritations in concentrated form. Further, in general, they are little tolerated by plants.

In contrast to the triorgano tin compounds, diorgano tin compounds are essentially less toxic but heretofore practically no activity against microorganisms such as fungi or bacteria has been determined. The minimum inhibition concentration (MIC), that is the amount of the pertinent compounds which can just prevent a multiplication of the microorganisms, has the following values for butyl tin compounds:

| Compound | MIC | |
|---|---|---|
| | *Aspergillus niger* | *Staphylococcus aureus* |
| Tri-n-butyl tin oxide | 0.4 ppm | 0.2 ppm |
| Di-n-butyl tin dichloride | 25.0 ppm | 12.5 ppm |

An object of the present invention is the preparation of agents comprising organotin compounds having a high bactericidal and fungicidal efficacy, but in which the disadvantages of the known agents have been overcome.

The agents according to the present invention are suitable for use as disinfecting agents, agents for the protection of wood, agents for imparting bactericidal and fungicidal properties to synthetic resins and textiles, and for use as biocidal coatings.

A feature of the present invention are agents which are characterized by a content of at least one diorgano tin compound of the general formula

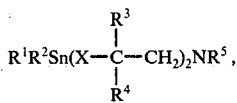

wherein $R^1$ and $R^2$ are straight chain, branched, or cyclic, optionally unsaturated, alkyl groups having 1-10 carbon atoms, or are aromatic groups; $R^3$ and $R^4$, taken alone, are the same or different and are hydrogen atoms or are straight chain or branched alkyl groups having 1-10 carbon atoms; $R^3$ and $R^4$, taken together, can be a doubly-bound oxygen atom; $R^5$ is a hydrogen atom or a straight-chain, branched, or cyclic, optionally unsaturated, alkyl group having 1-10 carbon atoms or is an optionally substituted aromatic group; and wherein X is oxygen or sulfur.

Particular embodiments are those wherein $R^3$ is hydrogen and X is oxygen and in which $R^1$ and $R^2$ are straight chain or branched, optionally unsaturated, alkyl groups having 2-6 carbon atoms or are aromatic groups.

Particularly preferred values of $R^1$ and $R^2$ are ethyl, i-butyl, n-butyl, or phenyl. Further preferred embodiments are those in which $(R^3 + R^4)$ is a doubly bound oxygen atom and in which the groups $R^1$, $R^2$, and $R^5$ are straight chain or branched alkyl groups having 2-6 carbon atoms or are mono- or bi-nuclear, optionally substituted, aromatic groups such as phenyl, naphthyl, m- and p-tolyl, m- and p-methoxyphenyl, or are benzyl or cyclohexyl, and wherein X is oxygen.

A further object of the invention is the use of the aforementioned agents as disinfecting agents, protective agents for wood, agents for imparting bactericidal and fungicidal properties to plastics, construction materials, textiles, or as biocidal coatings.

As preferred new compounds, the following are mentioned:

1,1,5-trimethyl-diptych-oxazstannolidin
1,1,3,7-tetramethyl-diptych-oxazstannolidin
1,1-diethyl-diptych-oxazstannolidin
1,1-diethyl-3,5,7-trimethyl-diptych-oxazstannolidin
1,1-diethyl-5-m-tolyl-diptych-oxazstannolidin
1,1-divinyl-5-methyl-diptych-oxazstannolidin
1,1-divinyl-3,5,7-trimethyl-diptych-oxazstannolidin
1,1-dibutyl-3,7-dimethyl-diptych-oxazstannolidin
1,1-di-isobutyl-5-methyl-diptych-oxazstannolidin
1,1-di-isobutyl-5-phenyl-diptych-oxazstannolidin
1,1di-isobutyl-5-m-tolyl-diptych-oxazstannolidin
1,1-di-isobutyl-5-p-tolyl-diptych-oxazstannolidin
1,1-di-isobutyl-5-cyclohexyl-diptych-oxazstannolidin
1,1-di-isobutyl-3,7-dimethyl-diptych-oxazstannolidin
1,1-di-isobutyl-3,5,7-trimethyl-diptych-oxazstannolidin
1,1-di-isobutyl-5-(5-acetamido-2-ethoxyphenyl)-diptych-oxazstannolidin
1,1-di-isobutyl-5-methyl-3,7-dioxo-diptych-oxazstannolidin
1,1-diphenyl-5-methyl-diptych-oxazstannolidin
1,1-diphenyl-5-cyclohexyl-diptych-oxazstannolidin
1,1-diphenyl-5-p-tolyl-diptych-oxazstannolidin
1,1-diphenyl-3,5,7-trimethyl-diptych-oxazstannolidin
1,1-di-isobutyl-diptych-oxazstannolidin
1,1-diphenyl-diptych-oxazstannolidin As further agents to be used according to the invention, the preparation of which is described by A. Tzschach, Z. anorg. allg. Chem. 404, 121 (1974) can be mentioned:

1,1-diethyl-5-methyl-diptych-oxazstannolidin
1,1-diethyl-5-propyl-diptych-oxazstannolidin
1,1,5-triethyl-diptych-oxazstannolidin
1,1-dibutyl-5-methyl-diptych-oxazstannolidin
1,1-dibutyl-5-ethyl-diptych-oxazstannolidin
1,1-dibutyl-5-propyl-diptych-oxazstannolidin
1,1-dibutyl-diptych-oxazstannolidin
1,1-dibutyl-5-phenyl-diptych-oxazstannolidin
1,1-dibutyl-5-m-tolyl-diptych-oxazstannolidin
1,1-dihexyl-5-methyl-diptych-oxazstannolidin
1,1-dihexyl-5-ethyl-diptych-oxazstannolidin
1,1-dioctyl-5-ethyl-diptych-oxazstannolidin
1,1-diethyl-5-methyl-diptych-thiazstannolidin
1,1-diethyl-5-propyl-diptych-thiazstannolidin
1,1,5-triethyl-diptych-thiazstannolidin
1,1-dibutyl-5-methyl-diptych-thiazstannolidin
1,1-dibutyl-5-ethyl-diptych-thiazstannolidin 1,1-dibutyl-5-propyl-diptych-thiazstannolidin
1,1-dihexyl-5-ethyl-diptych-thiazstannolidin
1,1-dioctyl-5-ethyl-diptych-thiazstannolidin.

Investigations of the structure of compounds of this type are known in the literature, for example Davies et al., J. Organomet. Chem. 39, 279-288 (1972); Zschunke et al., J. Organomet. Chem. 51, 197-201 (1973); Tzschach et al., Z. anorg. allg. Chem. 404, 121-128 (1974); and Zeldin et al., J. Organomet. Chem. 86, 369-382 (1975).

From these references, it is clear that a more or less strongly-coordinated linkage exists between the N- and the Sn-atom.

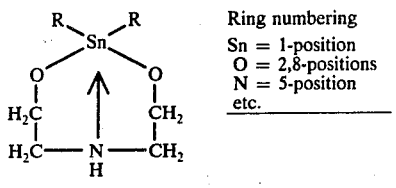

Ring numbering
Sn = 1-position
O = 2,8-positions
N = 5-position
etc.

These 1,1-disubstituted diptych-oxazstannolidins [Tzschach et al., Z. anorg. allg. Chem. 404, 121-128 (1974)] can also be designated as 1,1-disubstituted 2,8-dioxa-5-aza-1-stannabicyclo [3.3.0] octanes.

In analogy to the behavior of the stannatranes [Zeldin et al., J. Organomet. Chem. 86, 369-382 (1975)], there can be here also, depending on the polarity of the solvent, an equilibrium between the above-identified bicyclic form and a monocyclic form,

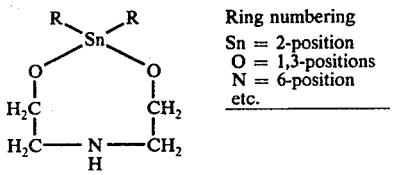

Ring numbering
Sn = 2-position
O = 1,3-positions
N = 6-position
etc.

This structure would then be named as a 2,2-disubstituted perhydro-1,3,6,2-dioxazastannocin or as a 2,2-disubstituted 2-stanna-1,3-dioxa-6-aza-cyclooctane.

The preparation of the diorgano tin compounds of the present invention can take place by the reaction of diorgano tin halides, diorgano tin oxides, or diorgano tin alkoxides with diethanolamines or dithioethanolamines [cf. equations (1) – (3)] or with iminodiacetic acid derivatives [see equation (4)]:

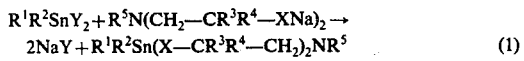
(1)

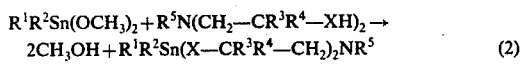
(2)

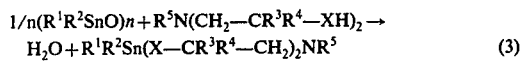
(3)

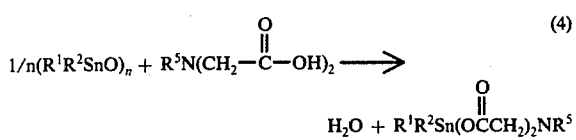
(4)

X = O,S
Y = Cl, Br

The diorgano tin compounds to be used according to the present invention can be used alone, in mixture with each other, or in mixtures with other active agents such as quaternary ammonium bases or phenolic compounds. The diorgano tin compounds are suitably used in the form of preparations such as solutions, dispersions, or dusts with the addition of inert liquid or solid carrier substances or diluents and optionally with the use of wetting agents, adhesion agents, emulsifiers, and/or dispersing agents.

Suitable liquid carriers are, for example, water or organic solvents such as ethanol, propanol, and xylene. As solid carriers, diatomaceous earth, argillaceous silicates, silica gel, kaolin, or talc are suitable.

The following surface-active agents can be mentioned as exemplary: calcium lignin sulfonate, polyoxyethylene-octylphenolether, naphthalene sulfonic acids, phenol sulfonic acids, formaldehyde condensates, fatty alcohol sulfates, and the alkali metal and alkaline earth metal salts of fatty acids.

The concentration of the active ingredient in these biocidal agents comprising a carrier and optional other substances can vary within relatively wide limits. It depends not only on the kind of microorganism to be combatted but also on the nature of the substrate (e.g. wood, textiles, etc.), and is between about 0.1 and 20 percent, calculated on the total weight of the biocidal agent. Since the diorgano tin compounds of the present invention are relatively water-insoluble, they can advantageously be used outdoors where they are exposed to weathering.

In contrast to the triorgano tin compounds such as tributyl tin oxide, which can severely damage the skin, even concentrated solutions of diorgano tin compounds have no skin-irritating action.

As has been shown by tests on plants, the phytotoxic effect of the diorgano tin compounds is likewise very small. Whereas plants are very strongly attacked by tributyl tin oxide, the agents of the present invention cause no damage.

A better understanding of the present invention and of its many advantages will be had by referring to the following specific Examples, given by way of illustration.

Among the Examples, Examples 1 and 2 relate to the preparation of diorgano tin compounds which, although generally considered biocidally ineffective, possess a high activity against bacteria and fungi as is evident from Tables I and II below.

Examples 3–23 relate to the preparation and properties of other diorgano tin compounds.

Example 24 illustrates a number of typical formulations combining an active agent and a carrier.

In Example 25, the efficacy of various of the agents described herein against bacteria and fungi is demonstrated by the use of a paper filter test. In the test, paper filters having a diameter of 5.5 centimeters are saturated with solutions (e.g. in butanol for Table I) of the compounds to be tested, in various concentrations. After air drying, the filter papers are placed on a nutritive agar layer. Subsequently, the agar is inoculated with a suspension of the test organism and the samples are incubated at 37° C.

The efficacy of the compounds is measured by the size of the zones of inhibition which form on the samples. The results are reported in Tables I–III.

In Examples 26 and 27, a textile and wood are respectively similarly treated and tested for biocidal activity.

EXAMPLE 1

1,1-di-isobutyl-diptych-oxazstannolidin 249 g of diisobutyl tin oxide and 105 g of di-ethanolamine are heated to boiling with 250 g of toluene for about 6 hours while cycling the water of reaction out of the system. Subsequently, the solvent is withdrawn under vacuum and about 320 g of a solid residue are obtained having a tin content of 35.1% (calc. = 35.3%).

EXAMPLE 2

1,1-di-phenyl-diptych-oxazstannolidin 289 g of diphenyl tin oxide are reacted with 105 g of diethanolamine in 250 g of toluene as described above. About 360 g of a solid slightly yellowish product are obtained. Tin content = 31.5% (calc. = 31.6%).

Both of the products of the foregoing Example are solid waxy substances which are difficultly soluble in water but, in contrast, soluble in many organic solvents.

EXAMPLE 3

1,1-di-isobutyl-5-phenyl-diptych-oxazstannolidin 121 g of diisobutyl tin oxide and 88 g of dioxyethyl aniline are reacted in 1000 ml of toluene as described above.

About 190 g of a coarse, almost while powder are obtained.

|  | % | Calculated |
|---|---|---|
| Analysis: C = | 51.92 | 52.46 |
| H = | 7.58 | 7.58 |

EXAMPLE 4

1,1-di-isobutyl-5-methyl-diptych-oxazstannolidin 67.4 g of diisobutyl tin dimethoxide are combined with 100 ml of dry toluene and 27.2 g of methyl diethanolamine in 150 ml of toluene are added with exclusion of moisture. During a heating step lasting about three hours, the methanol formed is distilled off together with the main portion of the toluene. Residual solvent is removed protectively under vacuum.

About 80 g of a light-brown liquid, which clouds slightly in moist air, are obtained.

|  | % | Calculated |
|---|---|---|
| Analysis: C = | 45.04 | 44.60 |
| H = | 8.65 | 8.35 |

EXAMPLE 5

1,1-diethyl-3,5,7-trimethyl-diptych-oxazstannolidin 59.35 g of diethyl tin dimethoxide and 36.57 g of methyl diisopropanolamine are treated as in Example 4 in a total of about 200 ml of toluene.

About 80 g of a slightly cloudy brown liquid are obtained. After setting of a small solids content, the liquid is decanted.

|  | % | Calculated |
|---|---|---|
| Analysis: C = | 41.97 | 41.02 |
| H = | 7.88 | 7.83 |
| Sn = | 36.55 | 36.86 |

EXAMPLE 6

1,1-diethyl-5-m-tolyl-diptych-oxazstannolidin

Proceeding again as in Example 4, 51.64 g of diethyl tin dimethoxide and 42.2 g of N,N-bis-(2-hydroxyethyl)-metatoluidine are reacted in a total of about 200 ml of toluene.

About 80 g of a solid cream-colored substance are obtained.

|  | % | Calculated |
|---|---|---|
| Analysis: C = | 47.58 | 48.68 |
| H = | 7.22 | 6.81 |
| Sn = | 31.70 | 32.07 |

EXAMPLE 7

1,1-di-isobutyl-5-cyclohexyl-diptych-oxazstannolidin 49.8 g of diisobutyl tin oxide and 37.4 g of N,N-bis-(2-hydroxyethyl)-cyclohexylamine are heated to boiling in about 200 ml of toluene while cycling water out of the system.

The solvent is removed under vacuum. Residual amounts of solvent remain in the substance and can be removed only with extreme difficulty. About 84.6 g of a weakly yellow somewhat sticky solid body are obtained.

|  | % | Calculated |
|---|---|---|
| Analysis: C = | 52.86 | 51.70 |
| H = | 9.15 | 8.92 |
| Sn = | 27.29 | 28.38 |

EXAMPLE 8

1,1-di-isobutyl-5-methyl-3,7-dioxo-diptych-oxazstannolidin 50.8 g of diisobutyl tin oxide and 30 g of methylimino diacetic acid are treated according to Example 7.

Somewhat more than the theoretical amount of a white solid product having an m.p. = 136°–137° C. is obtained.

EXAMPLE 9

1,1,5-trimethyl-diptych-oxazstannolidin 30.12 g of dimethyl tin dimethoxide and 17.01 g of methyl diethanolamine (143 m mol) were reacted in 100 ml of toluene as in Example 4. The product was obtained as a hard, solid, white mass in a yield of about 85 percent.

|  | % | Calculated |
|---|---|---|
| Analysis: C = | 32.09 | 31.62 |
| H = | 6.23 | 6.44 |
| Sn = | 43.50 | 44.64 |
| Cl = | <0.4 |  |

EXAMPLE 10

1,1,3,7-tetramethyl-diptych-oxazstannolidin 60.25 g of dimethyl tin dimethoxide and 38.06 g of diisopropanolamine were reacted according to Example 4 in 200 ml of toluene. The substance was obtained as a white, solid, lacquer-like mass in a yield of 79.5 g.

| | % | Calculated |
|---|---|---|
| Analysis C = | 35.65 | 34.33 |
| H = | 7.10 | 6.84 |

The substance contained < 0.7% of chloride.

EXAMPLE 11

1,1-diethyl-diptych-oxazstannolidin

After dissolving 3.68 g of sodium in 60 ml of methanol, 8.40 g of diethanolamine were added and 19.82 g of diethyl tin dichloride in 85 g of toluene was added dropwise to this solution. The methanol was distilled off and the solution was freed of precipitated NaCl through a G-4-frit. Yield = 18 g (80%). At 220° C., the substance sinters with decomposition.

| | % | Calculated |
|---|---|---|
| Analysis: Cl = | 0 | 0 |
| H = | 6.98 | 6.84 |
| Sn = | 41.50 | 42.40 |

EXAMPLE 12

1,1-divinyl-5-methyl-diptych-oxazstannolidin 25 g of methyldiethanolamine were added to 10.6 g of sodium dissolved in 110 ml of methanol. Freshly-distilled divinyl tin dichloride (51.22 g) was added dropwise to this solution. After the addition of 100 ml of toluene, methanol was distilled off and the solution was freed from NaCl using a D-4-frit. The solvent was distilled off using an oil pump vacuum at a bath temperature up to 80° C. The lightly-yellowish solid substance still showed only traces of chloride.

| | % | Calculated |
|---|---|---|
| Analysis: C = | 34.51 | 37.28 |
| H = | 6.19 | 5.91 |
| Sn = | 37.80 | 40.94 |

Yield = about 80 percent.

Under the conditions of the synthesis, a monovinyl tin compound was also formed.

EXAMPLE 13

1,1-divinyl-3,5,7-trimethyl-diptych-oxazstannolidin 8.6 g of sodium, 90 ml of methanol, 25 g of methyldiisopropanolamine, 41.38 g of divinyl tin dichloride, and 100 ml of toluene were treated according to Example 12. Also in this case, only traces of chloride were still detectable. The yield of lightly-yellowish soft substance was also about 80 percent.

| | % | Calculated |
|---|---|---|
| Analysis: C = | 40.21 | 41.55 |
| H = | 7.16 | 6.66 |

In this case also, a monovinyl tin species was formed.

EXAMPLE 14

1,1-dibutyl-3,7-dimethyl-diptych-oxazstannolidin 72.3 g of dibutyl tin dimethoxide and 32.69 g of diisopropanolamine were reacted according to Example 4 in 200 ml of toluene. The viscous liquid substance was obtained in a yield of 100 percent.

| | % | Calculated |
|---|---|---|
| Analysis: C = | 46.02 | 46.18 |
| H = | 8.61 | 8.58 |
| Sn = | 31.60 | 32.60 |
| Cl = | <0.2 | |

EXAMPLE 15

1,1-di-isobutyl-5-m-tolyl-diptych-oxazstannolidin 55.36 g of di-isobutyl tin dimethoxide (188 m mol) and 36.64 g of N,N-bis(2-hydroxyethyl)-m-toluidine (188 m mol) are added, with exclusion of moisture, to 100 ml of toluene. After heating for three hours, the methanol formed and a large portion of the toluene are distilled off. The remaining toluene is distilled off in vacuum. A cream-colored solid substance is produced in 100 percent yield (80 g).

| | % | Calculated |
|---|---|---|
| Analysis: C = | 53.10 | 53.54 |
| H = | 7.92 | 7.81 |
| N = | 3.33 | 3.29 |
| Cl = | 0.2 | 0 |
| Sn = | 27.55 | 27.85 |

EXAMPLE 16

1,1-di-isobutyl-5-p-tolyl-diptych-oxazstannolidin 49.78 g of di-isobutyl tin oxide (0.2 mol) and 39.0 g of N,N-dioxyethyl-p-toluidine (0.2 mol) were reacted according to Example 3 in 200 ml of toluene with vigorous stirring. The light yellow solid substance was obtained in a yield which was barely 100 percent of theory, was soluble in ethanol, and had a melting range of 186°–204° C.

| | % | Calculated |
|---|---|---|
| Analysis: C = | 53.71 | 53.55 |
| H = | 8.34 | 7.80 |
| Sn = | 26.80 | 27.85 |
| Cl = | 0 | 0 |

EXAMPLE 17

1,1-di-isobutyl-3,7-dimethyl-diptych-oxazstannolidin

With the difference that the i-butyl compound was used, the reaction was carried out using the same amount of reagents and the same procedures as in Example 14. The yield was 100 percent of a brownish viscous liquid substance.

| | % | Calculated |
|---|---|---|
| Analysis: C = | 45.91 | 46.18 |
| H = | 8.56 | 8.58 |
| Sn = | 32.65 | 32.60 |
| Cl = | 0 | 0 |

EXAMPLE 18

1,1-di-isobutyl-3,5,7-trimethyl-diptych-oxazstannolidin

The following substances were used in the following amounts as in Example 4: 189.1 g of di-isobutyl tin dimethoxide, 94.4 g of methyldiisopropanolamine, and 300 ml of toluene. Yield = 240 g (99% of theory).

| Analysis: | % | Calculated |
|---|---|---|
| C = | 47.11 | 47.64 |
| H = | 8.80 | 8.80 |
| Sn = | 31.43 | 31.40 |

EXAMPLE 19

1,1-di-isobutyl-5-(5-acetamido-2-ethoxyphenyl)-diptych-oxazstannolidin

By the azeotropic removal of the theoretical amount of water using 200 ml of toluene, and after removal of the toluene, a solid substance having a melting range of 173° C.-190° C., soluble in chloroform, is obtained from 49.8 g of di-isobutyl tin oxide and 56.5 g of 2-ethoxy-5-acetylamino-N,N-bis-hydroxyethyl-aniline (each 0.2 mol).

| Analysis: | % | Calculated |
|---|---|---|
| C = | 51.47 | 51.48 |
| H = | 7.43 | 7.46 |
| Sn = | 23.90 | 23.13 |

The yield is quantitative.

EXAMPLE 20

1,1-diphenyl-5-methyl-diptych-oxazstannolidin

The following were reacted according to Example 11: 2.4 g of sodium, 100 ml of methanol, 6.2 g of methyl diethanolamine, 17.7 g of diphenyl tin dichloride, and 100 ml of toluene. Yield = 19.1 g (95 percent of theory). The product is soluble in acetone and has a melting point of 68°-70° C.

| Analysis: | % | Calculated |
|---|---|---|
| C = | 51.81 | 52.35 |
| H = | 6.21 | 5.43 |
| Cl = | traces | 0 |
| Sn = | 29.30 | 30.43 |

EXAMPLE 21

1,1-diphenyl-5-cyclohexyl-diptych-oxazstannolidin 39 g of diphenyl tin oxide were treated according to Example 3 with 25.28 g of N-cyclohexyl-2,2'-amino-diethanol in 200 ml of toluene. The yellowish mass was soluble in toluene.

| Analysis: | % | Calculated |
|---|---|---|
| C = | 58.22 | 57.67 |
| H = | 7.39 | 6.38 |
| N = | 3.16 | 3.06 |

EXAMPLE 22

1,1-diphenyl-5-p-tolyl-diptych-oxazstannolidin 36.8 g of diphenyl tin oxide and 24.8 g of N,N-dioxyethyl-p-toluidine were reacted in 200 ml of toluene according to Example 3. The solid yellowish substance, which was quantitatively formed and which had a melting range of 60°-75° C., was soluble in chloroform.

| Analysis: | % | Calculated |
|---|---|---|
| Sn = | 25.45 | 25.46 |
| N = | 3.28 | 3.01 |

EXAMPLE 23

1,1-diphenyl-3,5,7-trimethyl-diptych-oxazstannolidin 65.78 g of diphenyl tin dichloride were added to a solution of 8.80 g of sodium in 100 ml of methanol. After the addition of 28.2 g of methyl diisopropanolamine in 200 ml of toluene, methanol was distilled off and NaCl was removed using a G-4-frit. After removal of the residual solvent in vacuum, the yield was 98 percent.

| Analysis: | % | Calculated |
|---|---|---|
| C = | 53.99 | 54.58 |
| H = | 6.00 | 6.03 |
| Cl = | <0.4 | 0 |
| Sn = | 28.00 | 28.39 |

EXAMPLE 24

The following, in which the amounts are in percent by weight, illustrate the formulation of suitable bactericidal and fungicidal agents:

a. 1,1-diphenyl-5-cyclohexyl-diptych-oxazstannolidin as a 2 percent solution in toluene.
b. 1,1-diphenyl-5-p-tolyl-diptych-oxazstannolidin as a 5 percent solution in chloroform.
c. 1,1-di-isobutyl-5-p-tolyl-diptych-oxazstannolidin as a 1 percent solution in ethanol.
d. 1,1-di-isobutyl-3,5,7-trimethyl-diptych-oxazstannolidin as a 1 percent aqueous emulsion containing 3 parts of an alkylarylpolyglycolether emulsifier.
e. 1,1-di-isobutyl-5-methyl-diptych-oxazstannolidin in a concentration of 2 percent on talc to form a strewable powder.
f. 1,1-di-isobutyl-diptych-oxazstannolidin as a 1 percent dilution in bleaching earth.
g. 1,1-dibutyl-5-methyl-diptych-thiazstannolidin as a 2 percent solution in ethanol.
h. 1,1-dibutyl-5-methyl-diptych-thiazstannolidin in a concentration of 3 percent on talc to form a strewable powder.

EXAMPLE 25

TABLE I

Test bacteria:
Bacillus subtilis ATCC 6633
Bacillus mesentericus ATCC 945
Escherichia coli ATCC 10,536

| Content of Active Agent on Filter | INHIBITION ZONES (mm) | | |
|---|---|---|---|
| | Bacillus subtilis | Bacillus mesentericus | Escherichia coli |
| 1) 0.5 % $(nC_4H_9)_2Sn(OCH_2CH_2)_2NH$ | 5 | 5 | 2 |
| 0.25% $(nC_4H_9)_2Sn(OCH_2CH_2)_2NH$ | 2–3 | 3–4 | 2 |
| 0.1 % $(nC_4H_9)_2Sn(OCH_2CH_2)_2NH$ | 2–3 | 3 | 1–2 |
| 2) 0.5 % $(iC_4H_9)_2Sn(OCH_2CH_2)_2NH$ | 12–15 | 8–9 | 4–6 |

EXAMPLE 25-continued

TABLE I

Test bacteria:
*Bacillus subtilis* ATCC 6633
*Bacillus mesentericus* ATCC 945
*Escherichia coli* ATCC 10,536

| Content of Active Agent on Filter | INHIBITION ZONES (mm) | | |
|---|---|---|---|
| | *Bacillus subtilis* | *Bacillus mesentericus* | *Escherichia coli* |
| 0.25% $(iC_4H_9)_2Sn(OCH_2CH_2)_2NH$ | 6–8 | 6–7 | 4 |
| 0.1 % $(iC_4H_9)_2Sn(OCH_2CH_2)_2NH$ | 5–6 | 4–5 | 3 |
| 3) 0.5 % $(C_6H_5)_2Sn(OCH_2CH_2)_2NH$ | 4 | 3 | 2 |
| 0.25% $(C_6H_5)_2Sn(OCH_2CH_2)_2NH$ | 2 | 2 | 1–2 |
| 0.1 % $(C_6H_5)_2Sn(OCH_2CH_2)_2NH$ | 1 | 1 | 1 |
| Comparison test | | | |
| 1) 0.5 % $(nC_4H_9)_2Sn(OOC\ CH_3)_2$ | 0 | 0 | 0 |
| 0.25% $(nC_4H_9)_2Sn(OOC\ CH_3)_2$ | 0 | 0 | 0 |
| 0.1 % $(nC_4H_9)_2Sn(OOC\ CH_3)_2$ | 0 | 0 | 0 |
| 2) Control (no active agent) | 0 | 0 | 0 |

The dibutyl-diptych-oxazstannolidins are extraordinarily effective against the test bacteria and, to be sure, not only against gram-positive but also, surprisingly, against gram-negative bacteria. This is all the more surprising as, normally, organo tin compounds are relatively ineffective against gram-negative bacteria.

TABLE II

Test fungus:
*Chaetomium globosum*

| Content of Active Agent on Filter | Inhibition Zones (mm) |
|---|---|
| 1) 1 % $(C_6H_5)_2Sn(OCH_2CH_2)_2NH$ | 10 |
| 0.5 % $(C_6H_5)_2Sn(OCH_2CH_2)_2NH$ | 9 |
| 0.25% $(C_6H_5)_2Sn(OCH_2CH_2)_2NH$ | 7 |
| 2) 1 % $(iC_4H_9)_2Sn(OCH_2CH_2)_2NH$ | 9 |
| 0.5 % $(iC_4H_9)_2Sn(OCH_2CH_2)_2NH$ | 8 |
| 0.25% $(iC_4H_9)_2Sn(OCH_2CH_2)_2NH$ | 6 |
| Comparison test | |
| 1) 1 % $(nC_4H_9)_2Sn(OOC\ CH_3)_2$ | 0 (Growth on the sample) |
| 0.5 % $(nC_4H_9)_2Sn(OOC\ CH_3)_2$ | 0 (Growth on the sample) |
| 0.25% $(nC_4H_9)_2Sn(OOC\ CH_3)_2$ | 0 (Growth on the sample) |
| 2) Control (no active agent) | 0 (Strong growth on the sample) |

Whereas the dibutyl tin diacetate used in the comparison test remains ineffective against the test fungus, the dibutyl- and diphenyl-diptych-oxazstannolidins show a high efficacy.

TABLE III

Test bacteria:
*Bacillus subtilis* ATCC 6633
*Bacillus mesentericus* ATCC 945
*Escherichia coli* ATCC 10,536

| Content of Active Agent on Filter | INHIBITION ZONES (mm) | | |
|---|---|---|---|
| | *Bacillus subtilis* | *Bacillus mesentericus* | *E. coli* |
| 4) 1 % 1,1-di-isobutyl-5-phenyl- | 10 – 12 | 5 | 10 |
| 0.5% diptych-oxazstannolidin | 10 | 4 | 4 – 5 |
| 0.2% | 8 – 9 | 3 – 4 | 2 – 4 |
| 5) 1 % 1,1-di-isobutyl-5-methyl- | 12 – 15 | 8 | 3 – 4 |
| 0.5% diptych-oxazstannolidin | 10 | 3 – 4 | 2 – 3 |
| 0.2% | 4 – 5 | 1 | 1 |
| 6) 1 % 1,1-diethyl-3,5,7-trimethyl- | 12 – 15 | 4 – 5 | 4 |
| 0.5% diptych-oxazstannolidin | 10 | 4 | 2 – 3 |
| 0.2% | 4 – 5 | 3 | 1 |
| 7) 1 % 1,1-di-isobutyl-5-m-tolyl- | 12 | 6 | 4 |
| 0.5% diptych-oxazstannolidin | 12 | 5 | 2 – 3 |
| 0.2% | 4 – 6 | 3 – 4 | 0 – 1 |
| Control (no active agent) | 0 | 0 | 0 |

EXAMPLE 26

Cotton fabric (275 g/m²) was treated with a xylene solution of 1,1-di-isobutyl-diptych-oxazstannolidin. The efficacy of the finish can be seen in the following Tables. Diameter of the Samples: 4.5 cm Test fungus: *Chaetomium globosum*

| Content of Active Agent in Sample (Weight Percent) | Growth on the Sample |
|---|---|
| 0 | strong |
| 2 | no growth |
| 1 | no growth |
| 0.5 | no growth |

Test bacterium: *Bacillus subtilis*

| Content of Active Agent in Sample (Weight Percent) | Zones of Inhibition (mm) |
|---|---|
| 0 | 0 |
| 2 | 10 – 12 |
| 1 | 10 – 12 |
| 0.5 | 10 |
| 0.1 | 4 |

EXAMPLE 27

Pine veneers were treated with a butanol solution of 1,1-di-isobutyl-diptych-oxazstannolidin and the efficacy of the finish against bacteria was tested.
Size of the Samples: 4 × 4 cm Test bacterium: *Bacillus subtilis*

| Content of Active Agent in Sample (Weight Percent) | Zones of Inhibition (mm) |
|---|---|
| 0 | 0 |
| 2 | 8 – 9 |
| 1 | 4 – 5 |
| 0.5 | 3 – 4 |

What is claimed is:

1. The method of killing bacteria and fungi which comprises bringing them into contact with a pesticidally-effective amount of a diorgano tin compound of the formula

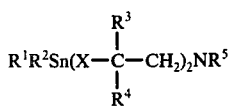

wherein $R^1$ and $R^2$ are alkyl having 1-10 carbon atoms, alkenyl having 1-10 carbon atoms, cycloalkyl, or aromatic; $R^3$ and $R^4$, taken alone, are the same or different and are hydrogen, alkyl having 1-10 carbon atoms or alkenyl having 1-10 carbon atoms; $R^3$ and $R^4$, taken together, are doubly bound oxygen; $R^5$ is hydrogen, alkyl having 1 to 10 carbon atoms, alkenyl having 1 to 10 carbon atoms, cycloalkyl, or a member selected from the group consisting of phenyl, naphthyl, m-tolyl, p-tolyl, m-methoxyphenyl, p-methoxyphenyl, benzyl, and 5-acetamido-2-ethoxy phenyl; and X is oxygen or sulfur.

2. A method as in claim 1 wherein $R^3$ is hydrogen and X is oxygen.

3. A method as in claim 2 wherein $R^1$ and $R^2$ are alkyl having 2-6 carbon atoms, alkenyl having 2-6 carbon atoms, or are aromatic.

4. A method as in claim 3 wherein $R^1$ and $R^2$ are ethyl, i-butyl, n-butyl, or phenyl.

5. A method as in claim 3 wherein $R^4$ and $R^5$ are hydrogen.

6. A method as in claim 4 wherein $R^4$ and $R^5$ are hydrogen.

7. A method as in claim 3 wherein $R^4$ and $R^5$ are alkyl having 1-6 carbon atoms, cycloalkyl, substituted aromatic or unsubstituted aromatic.

8. A method as in claim 7 wherein $R^5$ is phenyl, methyl, cyclohexyl, or m-tolyl.

9. A method as in claim 1 wherein $R^5$ is phenyl, methyl, cyclohexyl, or m-tolyl.

10. A method as in claim 1, wherein $R^3$ and $R^4$, taken together, are a doubly bound oxygen atom.

11. A method as in claim 10 wherein $R^1$, $R^2$, and $R^5$ are alkyl having 2-6 carbon atoms, mono-nuclear substituted aromatic, mono-nuclear unsubstituted aromatic, bi-nuclear substituted aromatic, bi-nuclear unsubstituted aromatic, benzyl or cyclohexyl.

12. A method as in claim 1 wherein said diorgano tin compound is a compound selected from the group consisting of 1,1-diethyly-5-methyl-diptych-oxazstannolidin;
1,1-diethyl-5-propyl-diptych-oxazstannolidin;
1,1,5-triethyl-diptych-oxazstannolidin;
1,1-dibutyl-5-methyl-diptych-oxazstannolidin;
1,1-dibutyl-5-ethyl-diptych-oxazstannolidin;
1,1-dibutyl-5-propyl-diptych-oxazstannolidin;
1,1-dibutyl-5-phenyl-diptych-oxazstannolidin;
1,1-dibutyl-5-m-tolyl-diptych-oxazstannolidin;
1,1-dihexyl-5-methyl-diptych-oxazstannolidin;
1,1-dihexyl-5-ethyl-diptych-oxazstannolidin;
1,1-dioctyl-5-ethyl-diptych-oxazstannolidin;
1,1-diethyl-5-methyl-diptych-thiazstannolidin;
1,1-diethyl-5-propyl-diptych-thiazstannolidin;
1,1-5-triethyl-diptych-thiazstannolidin;
1,1-dibutyl-5-methyl-diptych-thiazstannolidin;
1,1-dibutyl-5-ethyl-diptych-thiazstannolidin;
1,1-dibutyl-5-propyl-diptych-thiazstannolidin;
1,1-dihexyl-5-ethyl-diptych-thiazstannolidin;
1,1-dioctyl-5-ethyl-diptych-thiazstannolidin; and
1,1-dibutyl-diptych-oxazstannolidin.

13. A method as in claim 1 wherein $R^4$ is hydrogen and $R^5$ is alkyl having 1-6 carbon atoms, cycloalkyl, or a member selected from the group consisting of phenyl, naphthyl, m-tolyl, p-tolyl, m-methoxyphenyl, p-methoxyphenyl, benzyl, and 5-acetamido-2-ethyoxy phenyl; and X is oxygen or sulfur.

14. A method as in claim 1 wherein $R^1$ and $R^2$ are methyl, ethyl, n-butyl, isobutyl, vinyl, or phenyl; $R^3$ and $R^4$, taken alone, are hydrogen or methyl; $R^3$ and $R^4$, taken together, are a doubly bound oxygen atom; $R^5$ is hydrogen, methyl, phenyl, m-tolyl, p-tolyl, cyclohexyl, or 5-acetamido-2-ethoxyphenyl; and X is oxygen.

* * * * *